(12) United States Patent
Weber et al.

(10) Patent No.: US 11,173,033 B2
(45) Date of Patent: Nov. 16, 2021

(54) DOME STRUCTURE FOR IMPROVED LEFT VENTRICLE FUNCTION

(71) Applicant: BOSTON SCIENTIFIC SCIMED, INC., Maple Grove, MN (US)

(72) Inventors: Jan Weber, Maastricht (NL); Patricia McAfee, Galway (IE); Tim O'Connor, Galway (IE); Aiden Flanagan, Galway (IE); Omar Jarral, London (GB)

(73) Assignee: Boston Scientific Scimed, Inc., Maple Grove, MN (US)

( * ) Notice: Subject to any disclaimer, the term of this patent is extended or adjusted under 35 U.S.C. 154(b) by 433 days.

(21) Appl. No.: 16/139,760

(22) Filed: Sep. 24, 2018

(65) Prior Publication Data

US 2019/0091024 A1    Mar. 28, 2019

Related U.S. Application Data

(60) Provisional application No. 62/561,895, filed on Sep. 22, 2017.

(51) Int. Cl.
*A61F 2/24* (2006.01)

(52) U.S. Cl.
CPC .... *A61F 2/2487* (2013.01); *A61F 2002/2484* (2013.01); *A61F 2220/0016* (2013.01)

(58) Field of Classification Search
CPC ...... A61F 2002/2484; A61F 2220/0016; A61F 2/2487
See application file for complete search history.

(56) References Cited

U.S. PATENT DOCUMENTS

| | | | |
|---|---|---|---|
| 6,852,076 B2 | 2/2005 | Nikolic et al. | |
| 8,974,542 B2 | 3/2015 | Fujimoto et al. | |
| 9,198,757 B2 * | 12/2015 | Schroeder | A61B 17/00234 |
| 9,592,123 B2 | 3/2017 | Nikolic et al. | |
| 2002/0169360 A1 * | 11/2002 | Taylor | A61F 2/2481 600/37 |
| 2003/0050685 A1 | 3/2003 | Nikolic et al. | |
| 2008/0319254 A1 | 12/2008 | Nikolic et al. | |
| 2014/0100420 A1 | 4/2014 | Mortier et al. | |
| 2014/0179993 A1 | 6/2014 | Alexander et al. | |
| 2017/0363210 A1 | 12/2017 | Durst et al. | |

FOREIGN PATENT DOCUMENTS

DE        19933522 A1    9/2000

OTHER PUBLICATIONS

Invitation to Pay Additional Fees dated Jan. 1, 2019 for International Application No. PCT/US2018/052410.

* cited by examiner

*Primary Examiner* — Christine H Matthews
(74) *Attorney, Agent, or Firm* — Seager, Tufte & Wickhem LLP

(57) ABSTRACT

Device sand methods for improving cardiac function are provided. The device includes a dome structure having a top end with an engagement element disposed thereon. The dome structure is moveable from a first inside out configuration to a second deployed configuration, and the dome structure is biased in the second deployed configuration. The dome structure includes a plurality of anchor members disposed around a bottom open end of the dome structure.

15 Claims, 22 Drawing Sheets

DOME STRUCTURE FOR IMPROVED LEFT VENTRICLE FUNCTION

TECHNICAL FIELD

The disclosure relates generally to percutaneous medical devices and more particularly to percutaneous medical devices for implantation into the left ventricle (LV) of the heart.

BACKGROUND

Patients with chronic left ventricular dysfunction can, in some instances, be treated with a medical therapy with ACE inhibitors and beta blockers in an attempt to attenuate LV remodeling by modulation of neurohumoral activation. However post-myocardial infarction (MI) and heart failure patients commonly present with moderate mitral regurgitation (MR) despite this therapy and the efficacy of medical therapy in reducing functional mitral regurgitation (FMR) has not been well established.

Surgical ventricular restoration techniques such as plication have been used to resect the aneurysm and join healthy edges of myocardium. These are invasive techniques on relatively frail patients with limited clinical evidence to support their effectiveness (Surgical Treatment for Ischemic Heart Failure (STICH) trial). There is a continuing need for improved medical devices and minimally invasive methods to treat these patients to help reduce mitral regurgitation and restore cardiac function.

SUMMARY

In a first aspect, a device for improving cardiac function may comprise a dome structure having a top end with an engagement element disposed thereon, the dome structure moveable from a first inside out configuration to a second deployed configuration, the dome structure being biased in the second deployed configuration, and a plurality of anchor members disposed around a bottom open end, opposite the top end of the dome structure.

In addition or alternatively, and in a second aspect, the dome structure includes a plurality of elongate members connected to a central shaft, the engagement element disposed on the central shaft, each elongate member having a free end, wherein at least one of the plurality of anchor members is disposed on the free end of each elongate member.

In addition or alternatively, and in a third aspect, the dome structure includes a cover.

In addition or alternatively, and in a fourth aspect, the dome structure includes a wire mesh.

In addition or alternatively, and in a fifth aspect, the engagement element is a corkscrew extending from the top end toward the bottom open end of the dome structure in the second deployed configuration.

In addition or alternatively, and in a sixth aspect, the dome structure is made of a shape memory metal.

In addition or alternatively, and in a seventh aspect, the device further comprises a delivery catheter and an inner shaft slidingly disposed within the delivery catheter, wherein the dome structure is removably coupled to a distal end of the inner shaft in the first inside out configuration, wherein when the inner shaft is advanced out of a distal end of the delivery catheter, the dome structure automatically moves into the second configuration.

In addition or alternatively, and in an eighth aspect, the plurality of anchor members are barbs.

In addition or alternatively, and in a ninth aspect, the plurality of anchor members are hooks.

In addition or alternatively, and in a tenth aspect, when in the first inside out configuration, the hooks face outward away from a center of the dome structure, and when in the second deployed configuration, the hooks face inward toward the center of the dome structure.

In addition or alternatively, and in an eleventh aspect, the device further comprises a delivery catheter, an inner shaft slidingly disposed within the delivery catheter, a central shaft removably coupled to a distal end of the inner shaft, the central shaft having the engagement element disposed thereon, wherein the dome structure includes a plurality of elongate members having first ends fixed to the central shaft defining the top end of the dome structure, the plurality of elongate members automatically moveable from the first inside out configuration when constrained within the delivery catheter to the second deployed configuration when released from the delivery catheter, the plurality of elongate members being biased in the second deployed configuration, wherein the plurality of anchor members are disposed on second free ends of each of the plurality of elongate members.

In addition or alternatively, and in a twelfth aspect, the plurality of elongate members are made of a shape memory material.

In addition or alternatively, and in a thirteenth aspect, the engagement element is a corkscrew extending distally from the central shaft.

In addition or alternatively, and in a fourteenth aspect, the plurality of anchor members are hooks, wherein when in the first inside out configuration, the hooks face outward away from a center of the dome structure, and when in the second deployed configuration, the hooks face inward toward the center of the dome structure.

In addition or alternatively, and in a fifteenth aspect, a device for improving cardiac function may comprise a crimp device having a plurality of anchor members disposed thereon, a securing member, and a suture fixed to the securing member and connectable to the crimp device.

In addition or alternatively, and in a sixteenth aspect, the securing member is an external pledget.

In addition or alternatively, and in a seventeenth aspect, the securing member is an internal anchor having a suture eyelet and a plurality of anchors.

In addition or alternatively, and in an eighteenth aspect, a method for improving cardiac function may comprise inserting a distal end of a catheter into a patient's heart adjacent a region of heart wall to be treated, wherein the catheter includes an inner shaft slidable within the catheter and a dome structure removably coupled to a distal end of the inner shaft in a first inside out configuration, the dome structure having a top end with an engagement element disposed thereon and a plurality of anchor members disposed around a bottom open end of the dome structure, the dome structure moveable from the first inside out configuration to a second deployed configuration, the dome structure being biased in the second deployed configuration in which the dome structure defines a cavity. The method further comprises advancing the inner shaft distally at least partially out of the distal end of the catheter, fixing the engagement element on the dome structure to the heart wall in the region to be treated, withdrawing the catheter proximally from the dome structure, thereby allowing the dome structure to automatically move into the second deployed configuration, wherein movement of the dome structure into the second deployed configuration results in the anchor members engaging the heart wall and pulling the heart wall into the cavity defined by the dome structure.

In addition or alternatively, and in a nineteenth aspect, the engagement element is a corkscrew and the step of fixing the engagement element to the heart wall includes rotating the inner shaft to screw the corkscrew into the heart wall.

In addition or alternatively, and in a twentieth aspect, before inserting the catheter, the method includes applying a vacuum to an interior of the heart wall in the region to be treated to displace the heart wall inward, wherein fixing the engagement element to the heart wall includes fixing the engagement element to the displaced heart wall.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1A:
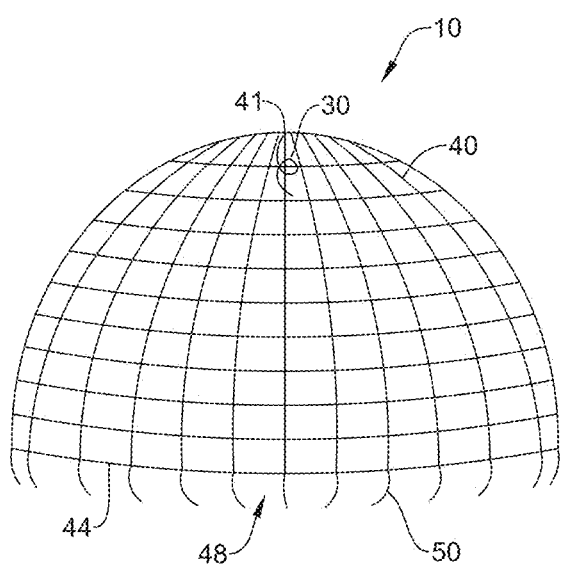
FIG. 1A is a perspective view of an exemplary device for improving cardiac function in a deployed configuration.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Figure 1B:
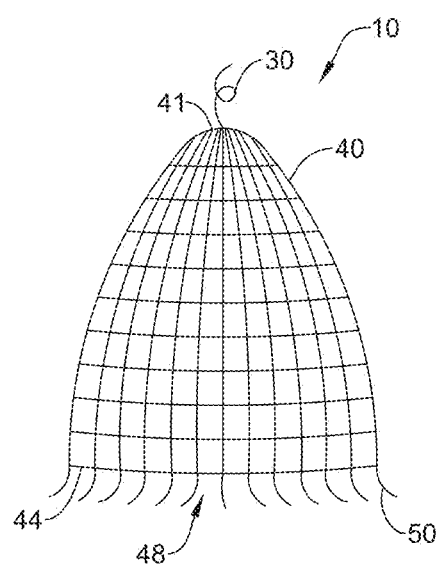
FIG. 1B illustrates the device of FIG. 1A in an inside out and compressed delivery configuration.

An embodiment of a device 10 for improving cardiac function is illustrated in FIGS. 1A and 1B. The device 10 includes a dome structure 40 having a top end 41 and an opposite bottom open end 44, an engagement element 30, and a plurality of anchor members 50 disposed around the bottom open end 44. The engagement element 30 is attached to the top end 41 of the dome structure 40. The dome structure 40 may be made of a shape memory material, such as a nitinol wire mesh. The dome structure 40 is biased toward an expanded deployed configuration, as shown in FIGS. 1A and 1s moveable into an inside out and compressed configuration, as shown in FIG. 1B, for delivery through a catheter. When the dome structure 40 is in the deployed configuration, shown in FIG. 1A, the anchor members 50, illustrated as hooks, face inward towards a center of the dome structure 40. This configuration allows the anchor members 50 to engage and pull tissue into the cavity 48 defined by the dome structure 40. When the dome structure 40 is in the inside out configuration, shown in FIG. 1B, the anchor members 50 face outwards (e.g., radially outwards), away from the dome structure 40. The engagement element 30 is illustrated as a corkscrew extending from the top end 41 toward the bottom open end 44 of the dome structure 40 in the second deployed configuration.

Figure 2A:
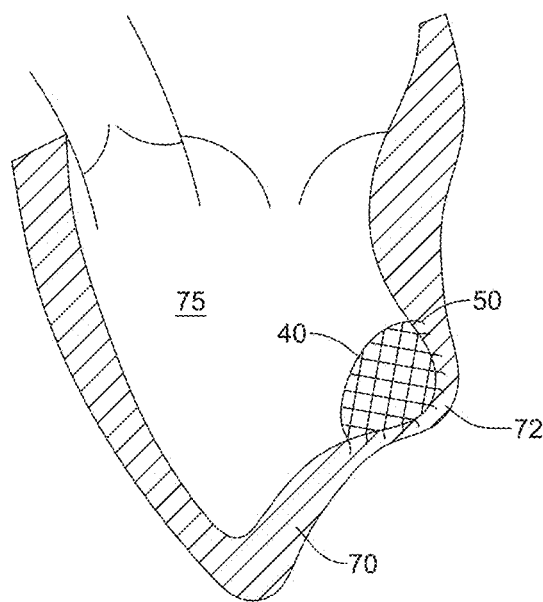
FIGS. 2A and 2B are partial cross sectional views illustrating the device of FIGS. 1A-1B during implantation in the heart.
Figure 2B:
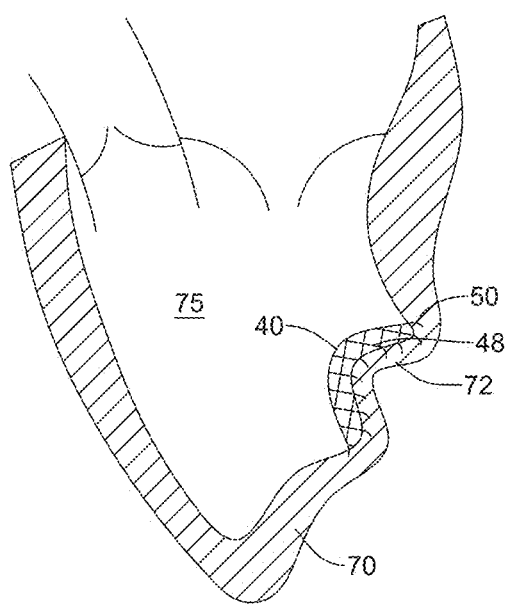

The device 10, in the inside out configuration (e.g., FIG. 1B), is delivered into the heart, for example in the left ventricle 75, via a catheter. The device 10 is positioned adjacent the myocardium 70, proximate (e.g., over) an outwardly bulging aneurysm 72. The engagement element 30 is fixed to the aneurysm 72, and the dome structure 40 is allowed to return to the biased deployed configuration, in which the anchor members 50 are embedded in the myocardium 70. FIG. 2A shows the anchor members 50 embedded in the myocardium 70 as the dome structure 40 begins to invert from the inside out delivery configuration to the biased deployed configuration. As the dome structure 40 returns to the biased deployed configuration, the aneurysm 72 is drawn into the cavity 48 defined by the dome structure, creating an inward bulge, as shown in FIG. 2B.

Figure 3:
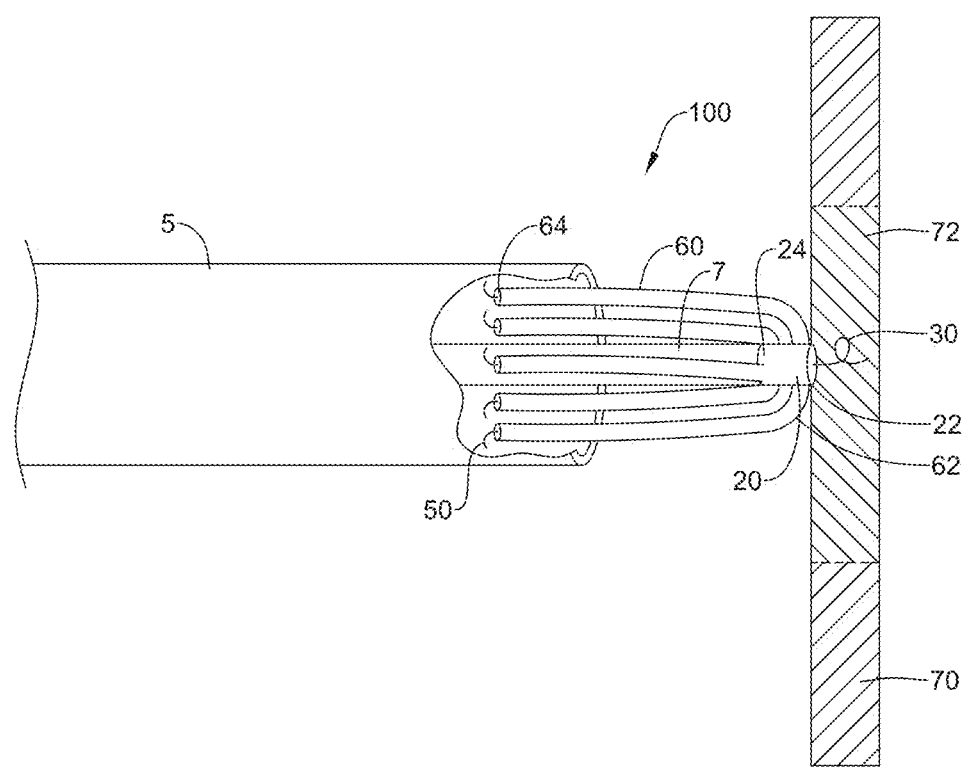
FIG. 3 is a partial cross sectional view of another exemplary device for improving cardiac function in a delivery configuration.

FIG. 3 illustrates an embodiment of a device 100 for improving cardiac function. The device 100 is removably coupled to the distal end of an inner shaft 7 in the inside out configuration. The inner shaft 7 is slidingly disposed within the delivery catheter 5 to deliver the device 100. In this embodiment, the dome structure is defined by a plurality of elongate members 60 having first ends 62 fixed to a central shaft 20 between the distal end 22 and the proximal end 24 of the central shaft 20. Alternatively, the elongate members 60 may be attached at the distal end 22 or the proximal end 24 of the central shaft 20. Each elongate member 60 has a second free end 64 with at least one anchor member 50 disposed thereon. The device 100 includes an engagement element 30 fixed to the distal end 22 of the central shaft 20. The central shaft 20 may be removably coupled to the distal end of the inner shaft 7. In some embodiments, the central shaft 20 may include an opening at the proximal end 24 and the distal end of the inner shaft 7 may have a friction fit within the opening. In other embodiments, the central shaft 20 and distal end of the inner shaft 7 may have a threaded engagement or a snap fit.

In the embodiment illustrated in FIG. 3, the engagement element 30 is a single corkscrew. In embodiments in which the central shaft 20 and inner shaft 7 are threadingly engaged, the corkscrew engagement element 30 may be provided such that rotation of the device 100 to insert the corkscrew engagement element 30 into tissue is in an opposite direction from the direction of rotation needed to uncouple the central shaft 20 from the inner shaft 7. That is, rotation of the corkscrew engagement element 30 into the myocardium 70 may, in an embodiment, uncouple the device 100 from the inner shaft 7. The engagement element 30 may be any structure that secures the device 100 to tissue, such as at least one corkscrew, hook, barb, or other projection.

The anchor members 50 are illustrated in FIGS. 1A-6 as hooks. In other embodiments, the anchor members 50 may be barbs, prongs, or any other structure configured to engage tissue. The anchor members 50 may have sharp free ends to penetrate the myocardium 70. Further, the anchor members may include multiple hooks, barbs, prongs, etc., disposed at a single location. For example, when the dome structure 40 includes a plurality of elongate members 60 as illustrated in FIGS. 3-6, each elongate member 60 may have at least one anchor member 50 disposed on the free end 64 of the elongate member 60.

For implantation, the device 100 is placed in a first inverted or inside out and collapsed configuration and mounted on the distal end of an inner shaft 7 and disposed within a delivery catheter 5. The delivery catheter 5 with inner shaft 7 and device 100 disposed therein, are inserted into the heart. When the distal end of the delivery catheter 5 is adjacent the aneurysm 72 in the myocardium 70, the inner shaft 7 is advanced distally partially out of the distal end of the delivery catheter 5. The engagement element 30 is affixed to the myocardium 70 in the region of the aneurysm 72, such as in the center of the aneurysm 72 as shown in FIG. 3. In the embodiment with a corkscrew engagement element 30, the inner shaft 7 may be rotated to screw the device 100 into the aneurysm 72. Once the engagement element 30 is fixed to the aneurysm 72, the delivery catheter 5 may be withdrawn proximally over the device 100, as shown in FIG. 3.

Figure 4:
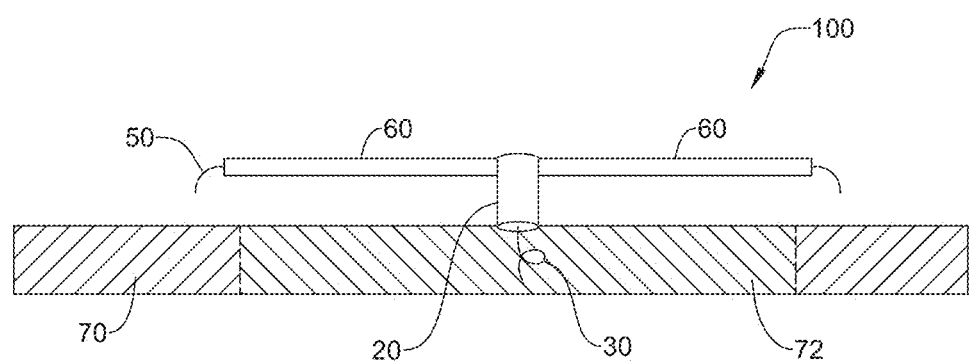
FIG. 4 is a partial cross sectional view of the device of FIG. 3 in a partially implanted configuration.
Figure 5:
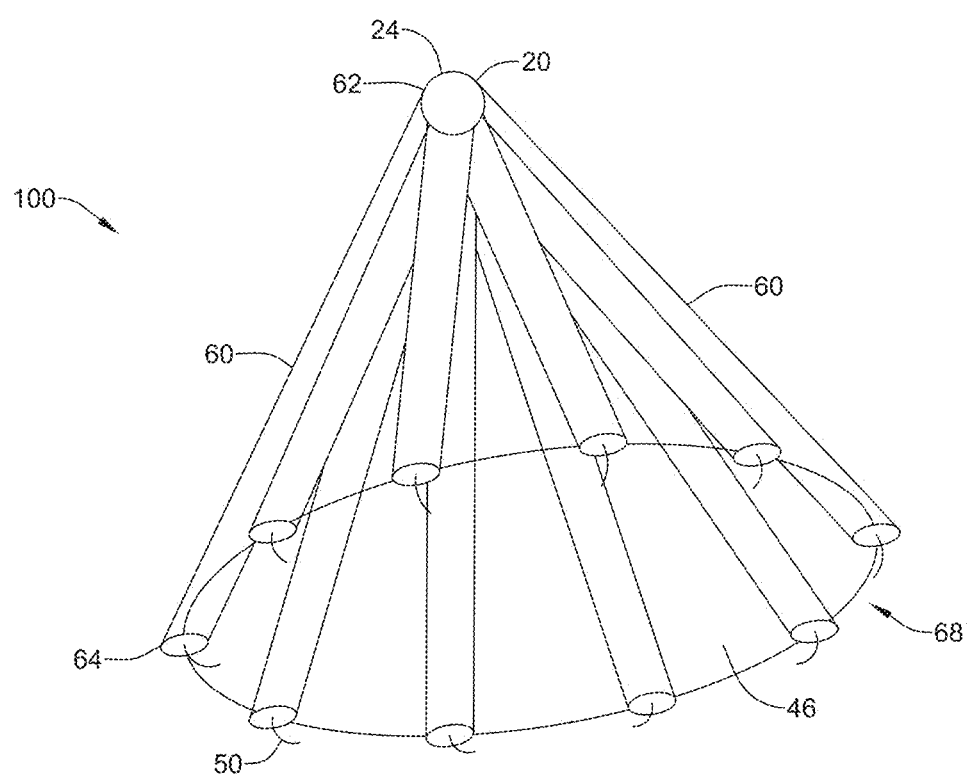
FIG. 5 is a perspective view of the device of FIG. 3 in an implanted configuration.

Movement of the device 100 between the first inside out delivery configuration to the second deployed configuration is illustrated in FIGS. 3-6. In an example, the elongate members 60 are made of a shape memory material, such as nitinol, and are inverted into a first inside out delivery configuration when loaded into the delivery catheter 5, as shown in FIG. 3. In the first inside out delivery configuration, the anchor members 50, such as the hooks shown in FIG. 3, face outward, radially away from a center of the device 100 and the inner shaft 7. As the device 100 is moved out of the confines of the delivery catheter 5, the elongate members 60 automatically move into the biased second deployed configuration. FIG. 4 shows the device 100 in a partially deployed configuration, with the elongate members 60 part way through their movement from the first inside out configuration shown in FIG. 3 to the biased second deployed configuration shown in FIG. 5. As shown in FIG. 4, the elongate members 60 have moved from the inverted dome in FIG. 3 to an essentially flat configuration where the anchor members 50 are poised to engage the myocardium 70. The device 100 may be positioned such that the anchor members engage healthy myocardium 70 outside the region of the aneurysm 72.

Figure 6:
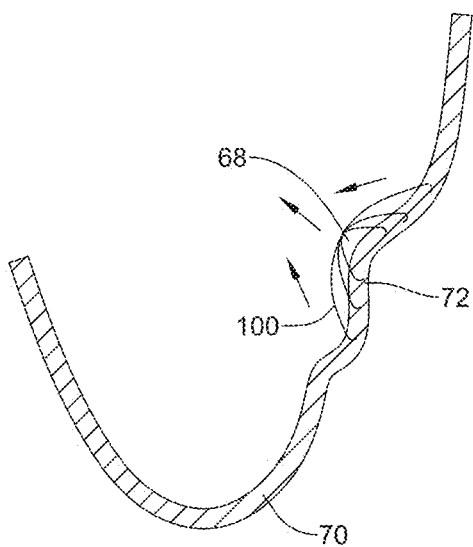
FIG. 6 is a cross sectional view illustrating the device of FIG. 3 implanted in the heart.

As the elongate members 60 continue moving into the second deployed configuration, the device 100 moves in the direction shown by the arrows in FIG. 6, the anchor members 50 become embedded in the myocardium 70 and pull the tissue into the cavity 68 defined by the dome structure. In the second deployed configuration, the anchor members 50 face inward (e.g., radially inward), toward the center of the device 100 and a central axis of the central shaft 20. The anchor members 50 are configured to engage healthy myocardium 70 and pull the aneurysm 72 into the cavity 68 defined by the device 100 when the elongate members 60 are in the second deployed configuration. The device 100 displaces the heart wall inward (e.g., within/toward the cavity 68), reducing left ventricle volume and heart wall stress. The device further displaces the papillary muscles upwards towards the annulus to reduce leaflet tethering, and connects healthy myocardium to healthy myocardium for improved contractility. The device 100 causes the normally outward bulging aneurysm 72 to be transformed into an inwardly bulging region as seen in FIG. 6. During the contraction of the left ventricle, this region will bulge even further inward, helping reduce the systolic volume of the left ventricle.

Catheter insertion of the device 100 may be performed after manipulation of the left ventricle wall by internal vacuum and/or external pressure. An internal vacuum can be applied through a suction catheter to displace the left ventricle wall into the desired position. The device 100 may be unsheathed to release the anchor members 50 into the endocardium and the dome structure 40 maintains the inward pull force on the left ventricle wall. Alternatively, external pressure can be applied to displace the left ventricle wall through a ball nosed catheter accessed through the pericardium by mini-thoracotomy access. The dome structure 40 may be unsheathed on the endocardial surface as the pressure is applied on the epicardium.

In some embodiments, the dome structure 40 may include a cover 46. In the embodiment illustrated in FIG. 5, the cover 46 is disposed over the plurality of elongate members 60, extending between fixed first ends 62 and free ends 64 of the elongate members 60. The cover 46 may be disposed on the outside or inside of the elongate members 60. The cover 46 may be a flexible fabric, wire mesh or polymer material that expands and contracts as the elongate members 60 move between the first inside out configuration when the device 100 is in the catheter, to the second deployed configuration. The plurality of anchor members 50 may be free of the cover 46.

Figure 7:
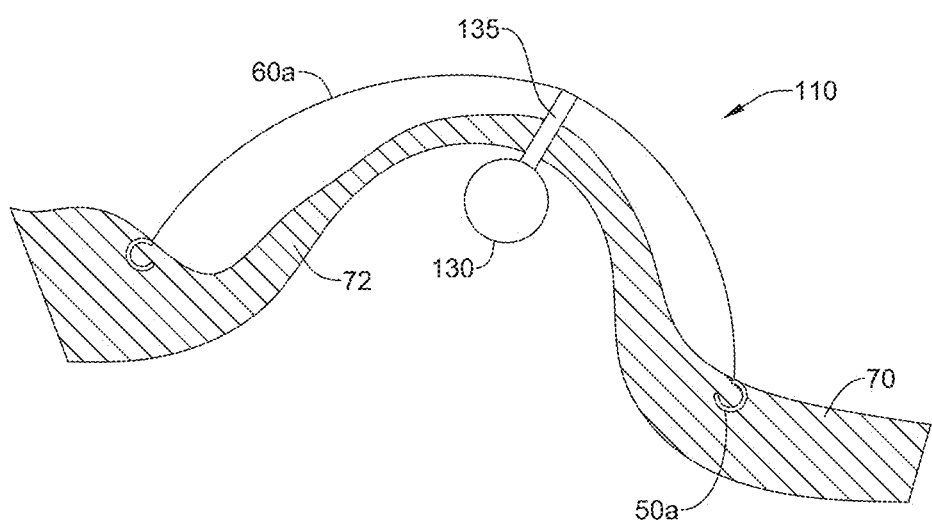
FIG. 7 is a cross sectional view of an exemplary device for improving cardiac function implanted in the heart.

FIG. 7 shows another device 110 affixed to the myocardium 70. The device 110 includes a plurality of elongate members 60a with anchor members 50a at free ends thereof, similar to the device 100 shown in FIGS. 3-6. The device 110 may include an external anchor 130 configured to be disposed on the epicardial surface of the heart. The external anchor 130 may be a plate, ball, or other shape sized larger than an opening disposed through the heart wall. The external anchor 130 may be connected to the plurality of elongate members 60a by a tube or post 135. In some examples, the external anchor 130 may be an inflatable structure such as a balloon, and the post 135 may include an inflation lumen. The balloon may be inflated from within the heart. In some examples, the balloon may be inflated with a hardening or solidifying material, such as epoxy, so the balloon retains its size and shape after inflation. During implantation, a hole may be made through the heart wall in the region of the aneurysm 72, the balloon external anchor 130 and post 135 may be inserted through the hole, the balloon external anchor 130 may be inflated to lock the device 110 in place over the aneurysm, and the plurality of elongate members 60a may then be released from the delivery catheter, allowing the anchor members 50a to engage the endocardial surface of the heart surrounding the aneurysm, as with the device 100 shown in FIGS. 3-6. As the elongate members 60a exit the delivery catheter, they move into the biased configuration and the anchor members 50a become embedded in the heart wall, pulling the aneurysm 72 into the dome formed by the elongate members 60a, as shown in FIG. 7.

In another example, the entire device 110 may be mounted from the pericardium. A hole may be made through the pericardium, elongate members 60a may be pushed through the hole into the heart, after which the elongate members 60a would unfold into the left ventricle. Once unfolded, the elongate members 60a with anchor members 50a embedded in the heart wall, would pull the aneurysm 72 inwards. The external anchor 130 sized larger than the hold through the heart wall prevents the entire device entering the heart chamber and secures the device 110 to the heart wall.

Figure 8A:
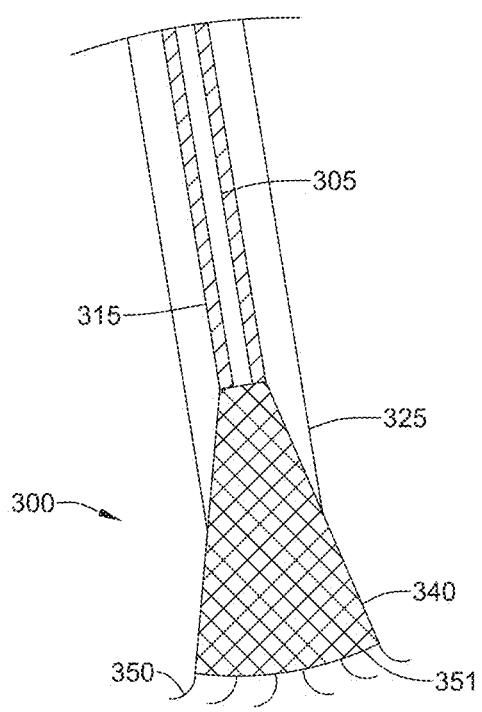
FIGS. 8A-8D are cross sectional views of an exemplary device for improving cardiac function.
Figure 8B:
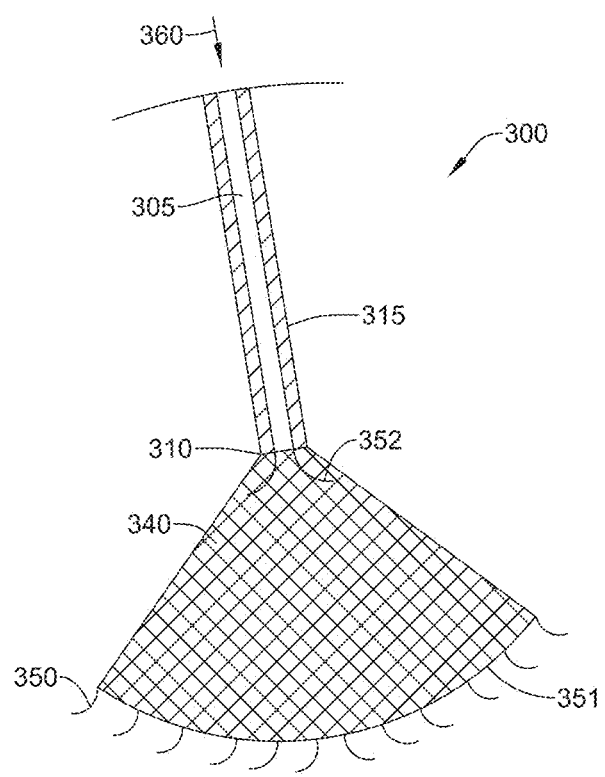
Figure 8C:
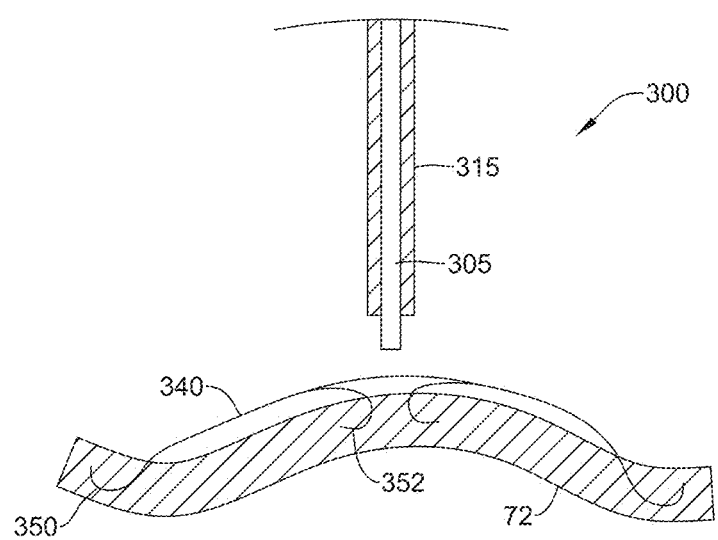
Figure 8D:
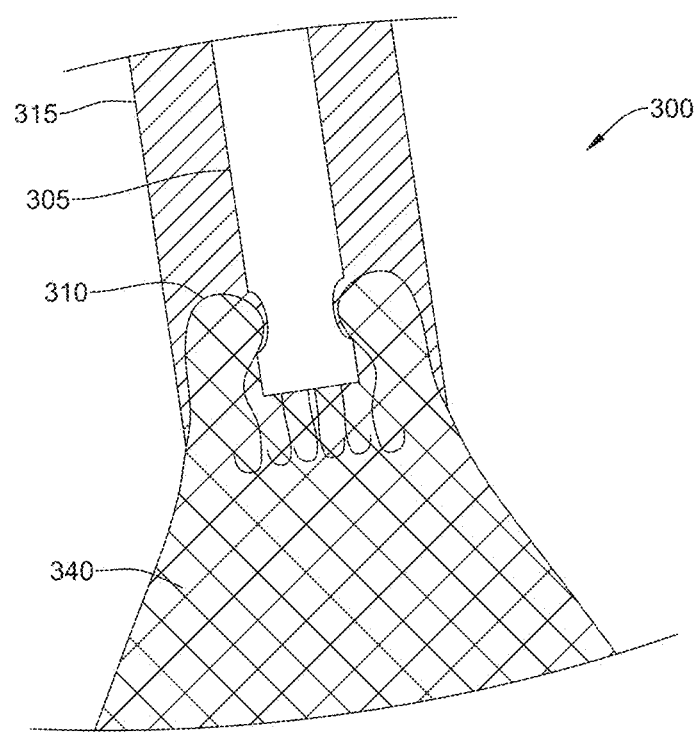

FIGS. 8A-8D illustrate an example of a device 300 including a shape memory mesh or braided stent 340 with a plurality of anchor members 350 disposed on a distal end 351 thereof, and a plurality of anchor members 352 disposed on a proximal end 310 thereof, as shown in FIG. 8B. The device 300 may be biased in a tubular stent configuration. For delivery, the proximal end 310 of the device 300 may be mounted between an inner catheter 305 and an intermediate sheath 315, as shown in FIG. 8D. An outer sheath 325 may be disposed over the stent, holding it in a contracted state for delivery. The device 300 is delivered to the aneurysm 72, and the outer sheath 325 is partially withdrawn proximally, revealing the anchor members 350 on the distal end, as shown in FIG. 8A. As the outer sheath 325 is withdrawn and the device expands, the anchor members 350 become embedded in the myocardium. Once the outer sheath 325 is withdrawn from the device, the proximal end 310 of the stent 340 is pushed distally with the inner catheter 305 and intermediate sheath 315, as indicated by arrow 360 in FIG. 8B, until the anchor members 352 engage the aneurysm 72. The intermediate sheath 315 is then withdrawn proximally, releasing the proximal end 310 of the stent 340, as shown in FIG. 8C. Once deployed, the device will attempt to regain its shape memory configuration of a tubular element, pulling the anchor members 352 into the interior of the stent 340.

Figure 9:
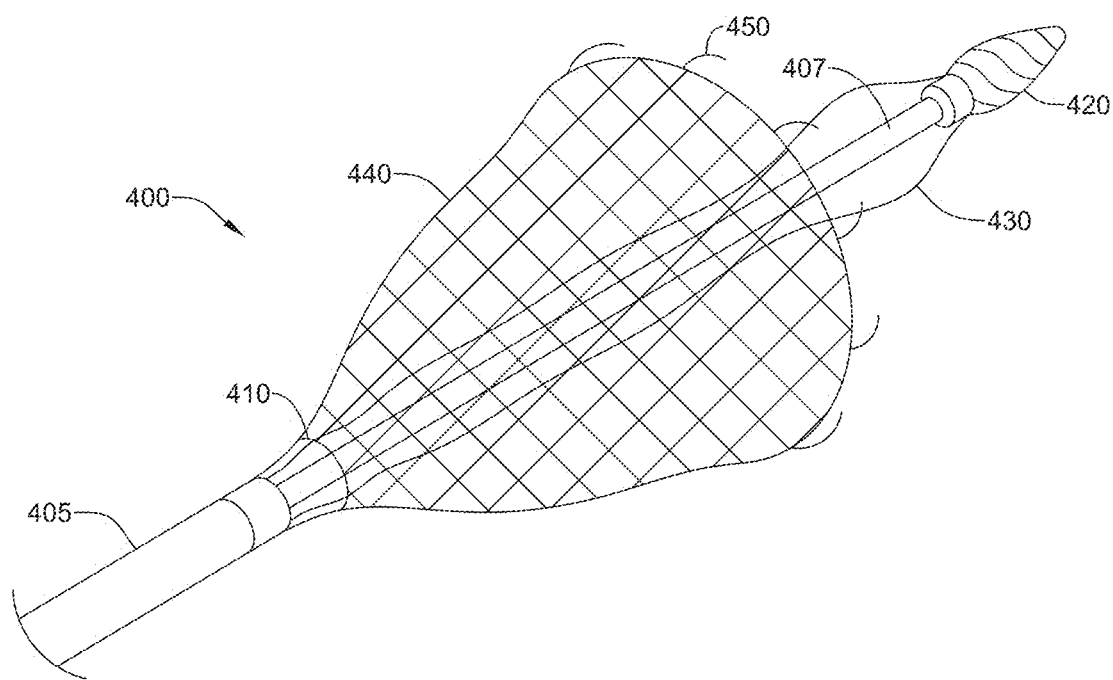
FIG. 9 is a perspective view of an exemplary device for improving cardiac function.

A further example device 400 is shown in FIG. 9. A braided or woven stent 440 may have a plurality of anchor members 450 such as hooks or barbs, disposed on a first end of the stent 440. For delivery, the stent 440 may be mounted on a delivery shaft 407 with a threaded drill head 420 disposed at the distal end thereof. The drill head 420 is removably attached to the distal end of the delivery shaft 407, for example, by a threaded connection. The threading of the threaded connection may be in the opposite direction as the threading on the drill head 420 such that rotating the delivery shaft 407 to the right will screw the drill head 420 into the myocardium (e.g., 72), and then rotating the delivery shaft 407 to the left will detach the drill head 420 from the delivery shaft 407, leaving the drill head 420 in the heart wall.

The stent 440 may have a ring 410 disposed on the proximal end of the stent 440. A plurality of wires 430 extend from the drill head 420 through the ring 410 and further through the delivery system to the proximal end of the delivery system. In use, the drill head 420 is inserted into the myocardium by rotating the delivery shaft 407 in a first direction, and then the user pulls back a delivery sheath 405, allowing the stent 440 with anchor members 450 to unfold as shown in FIG. 9. Pushing the stent 440 against the myocardium and then pulling backwards forces the anchor members 450 to be embedded into the myocardium. Next, the user rotates the delivery shaft 407 in a second direction opposite the first direction, to detach the delivery shaft 407, leaving the drill head 420 in the myocardium. The user then pulls the wires 430 through the ring 410 to pull the heart wall into an inward dome within the stent 440. Finally, the user secures the wires 430 on the proximal side of the ring 410 and removes the delivery system.

Figure 10A:
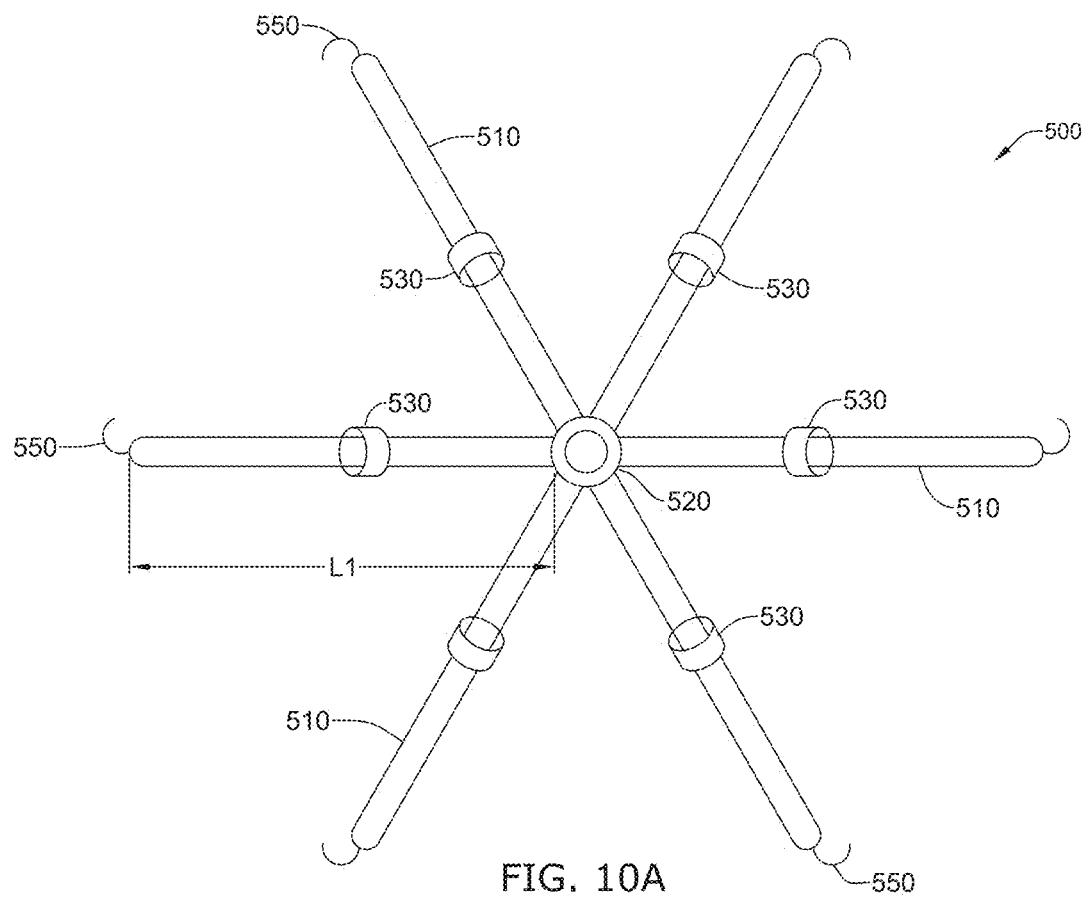
FIGS. 10A and 10B are perspective views of an exemplary device for improving cardiac function.
Figure 10B:
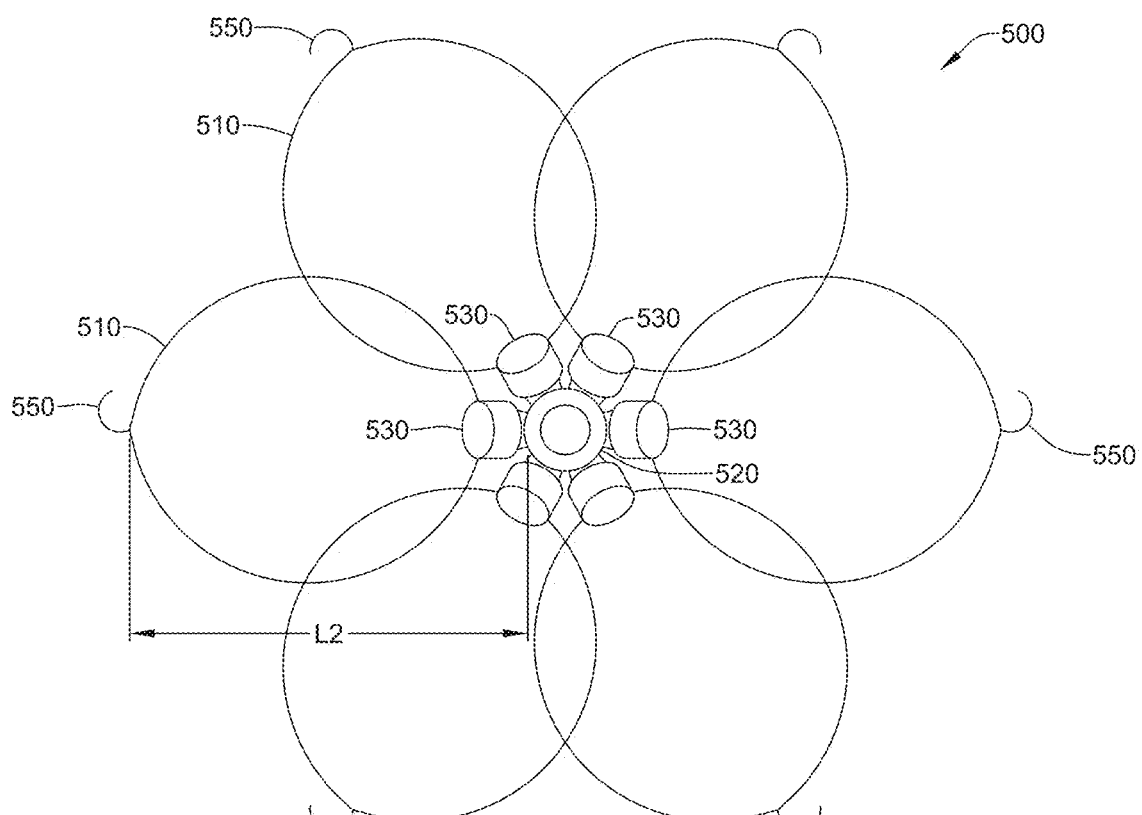

Device 500 is shown in FIGS. 10A and 10B. Device 500 includes a dome structure defined by a plurality of wire loops 510 connected to one another at a central ring 520 forming the top of the dome. The central ring 520 is configured to be removably disposed on the distal end of a delivery shaft, such as the inner shaft 7 shown in FIG. 3. The wire loops 510 each have at least one anchor member 550 on a distal end thereof. Each wire loop 510 is biased toward an expanded configuration, as shown in FIG. 10B. Each wire loop 510 has a slideable band 530 disposed thereon, constraining the wire loop 510 in an elongated configuration having a first length L1, as shown in FIG. 10A. The band 530 is configured to slide from a first position at a middle portion of the wire loop 510, shown in FIG. 10A, to a second position adjacent the central ring 520, as shown in FIG. 10B. Sliding the band 530 to the second position allows the wire loop 510 to expand in width, resulting in a second length L2 that is shorter than the first length L1.

The device 500 may include an engagement element (not shown) similar to the corkscrew shown in FIGS. 1A and 1B. The device 500 may be delivered into the heart in the same manner as the devices 100 and 100 described above. FIGS. 10A and 10B show the device 500 in a partially deployed configuration, with the wire loops 510 having moved from an inverted dome to an essentially flat configuration for engaging the heart wall tissue. After the anchor members 550 become embedded in the myocardium, the bands 530 in the middle of the wire loops as, shown in FIG. 10A, are moved to the second position adjacent the central ring 520 at the proximal end of the device, as shown in FIG. 10B. This allows the wire loops 510 to move from a parallel extended configuration, shown in FIG. 10A to a rounded contracted configuration as shown in FIG. 10B, shortening the distance between the anchor members 550 and the central ring 520, contracting the dome and pulling the myocardium into the dome. Further, the overlapping circles of the wire loops 510 creates a stronger overall mesh.

Figure 11:
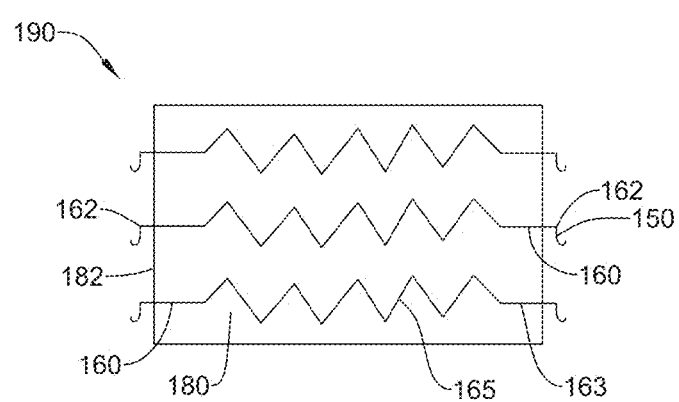
FIG. 11 is a top view of an exemplary device for improving cardiac function.

The device 190 shown in FIG. 11 is an alternative device for bridging an aneurysm. The device 190 includes a plurality of elongate spring members 160 disposed on or embedded within a patch 180. The patch 180 may be made of a biodegradable material such as polylactic acid (PLA). Each spring member 160 has an anchor member 150 disposed at each terminal end 162 thereof. The spring members 160 may include at least one substantially linear regions 163 and at least one compressible region 165. In the device shown in FIG. 11, the spring members 160 each include two linear regions 163 separated by a single compressible region 165. In other embodiments, the device 190 may include a plurality of compressible regions 165 interspersed with a plurality of linear regions 163. Alternatively, the entire spring member may be a single compressible region 165. The compressible region 165 may be a two dimensional spring such that it lays flat on the patch 180. The spring members 160 may be embedded within the patch 180, with only the anchor members 150 extending beyond, and not embedded within, the patch 180. In some embodiments, the anchor members 150 extend laterally beyond the border 182 of the patch 180, as shown in FIG. 11. In other embodiments, the patch 180 may extend beyond the anchor members 150, with the spring members 160 embedded within the patch and the anchor members 150 extending above the patch 180 (not shown). The spring members 160 may be made of a shape memory material such as nitinol. The spring members 160 may be embedded in the patch 180 in a compressed state. The plurality of spring members 160 may all be oriented in one direction such that they are substantially parallel, as shown in FIG. 11.

Figure 12:
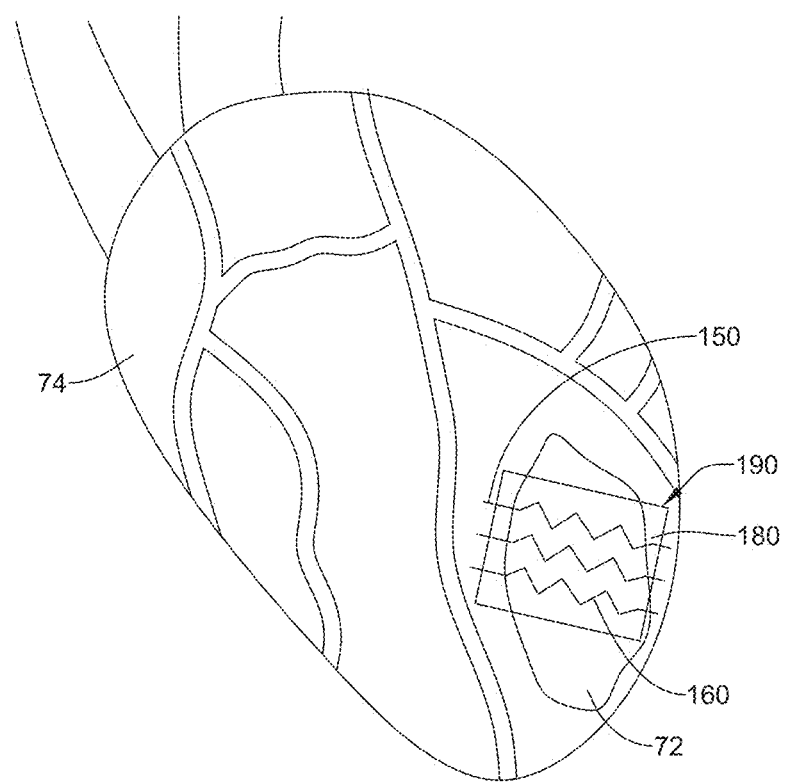
FIG. 12 is a perspective view of the device of FIG. 11 implanted on the heart.

The device 190 may be fixed to the epicardial surface of the heart 74 across an aneurysm 72 by embedding the anchor members 150 on the ends of the spring members 160 into healthy tissue adjacent opposite sides of the aneurysm 72, as shown in FIG. 12. Once the patch 180 degrades, the spring members 160 apply compressive force to pull the healthy regions together, preventing the aneurysm from bulging outward. The device 190 may be delivered to the epicardial surface through minimally invasive access by a left mini thoracotomy. The device 190 may alternatively be delivered onto the endocardial surface of the heart.

Figure 13:
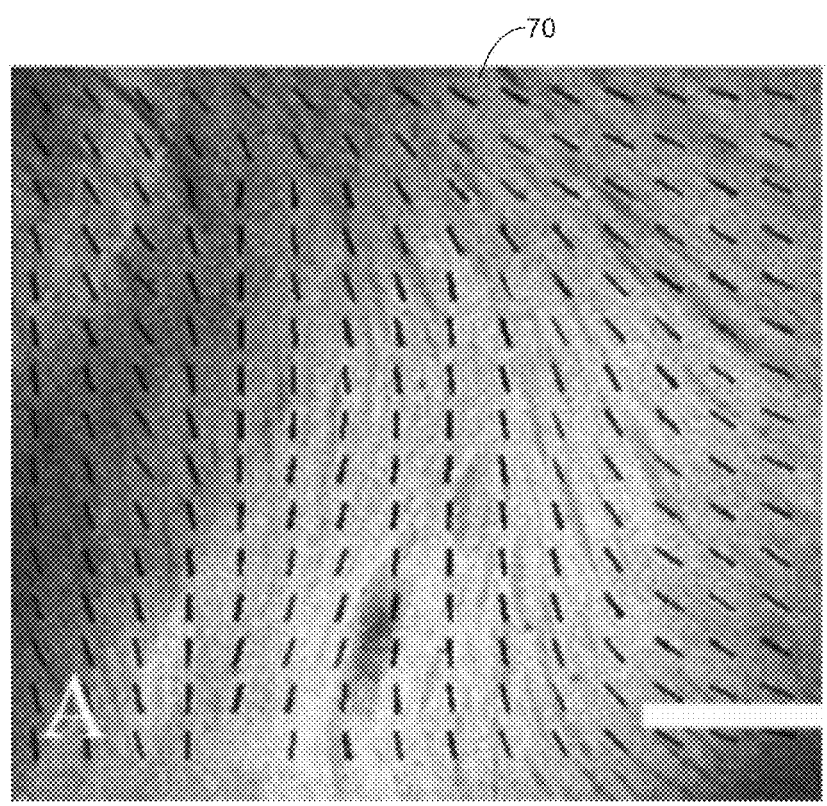
FIG. 13 illustrates the natural heart tissue fiber orientation.

The device 190 may be placed such that the spring members 160 conform with the natural myocardium 70 fiber orientation as shown by the dashed lines in FIG. 13. This orientation differs on the subendocardium and subepicardium of the left ventricle.

Figure 14:
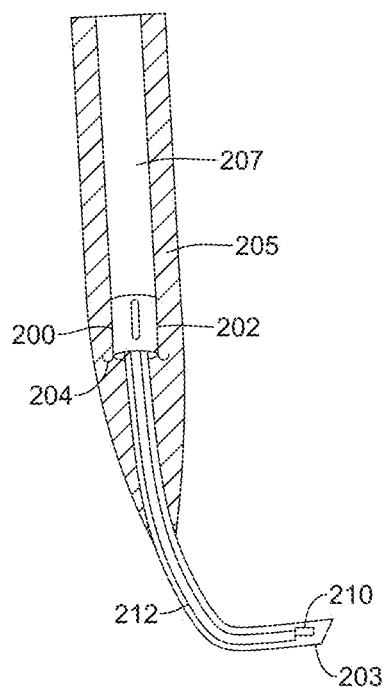
FIG. 14 is a cross sectional view of an example of a device for improving cardiac function.

Another approach to achieve percutaneous left ventricle plication and bridge healthy myocardium to healthy myocardium cross an aneurysm is to use a suture delivery catheter 205 with a preloaded crimp device 200, shown in FIG. 14. The crimp device 200 includes a crimp body 202 with a plurality of anchor members 204 disposed thereon, and a securing member such as an external pledget 210 connectable to the crimp body 202 with at least one suture 212. The suture 212 may be fixed to the pledget 210 and connectable to the crimp body 202. The anchor members 204 may be hooks, barbs, or corkscrews. The catheter 205 includes an inner sheath 207 configured to move the crimp body 202 out of the catheter 205, and an inner needle 203 pre-loaded with the pledget 210 and sutures 212.

Figure 15:
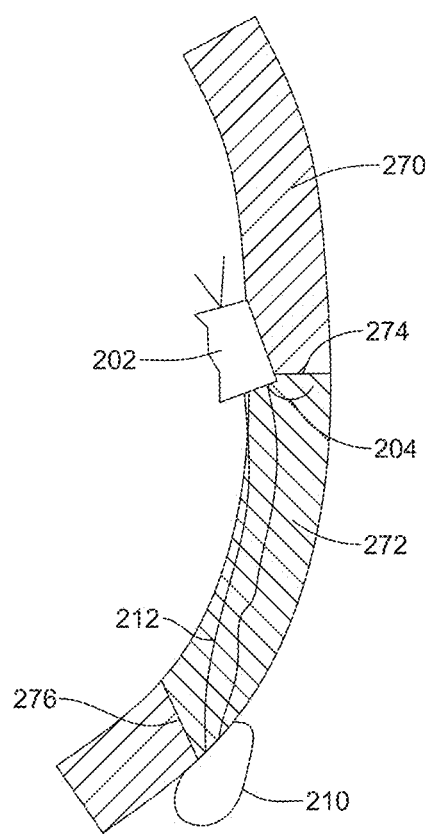
FIG. 15 is a cross sectional view illustrating the device of FIG. 14 implanted in the heart.

The catheter 205 is steered towards the left ventricle and an echocardiogram is used to determine the boundary of ischemic tissue. The inner needle 203 of the catheter 205 penetrates the myocardium 270 at the proximal boundary 274 of the ischemic tissue 272 and is advanced to the distal boundary 276 of the ischemic tissue 272 where the pledget 210 and suture 212 are deployed on the epicardium, as shown in FIG. 15. The inner needle 203 is retracted and a crimp body 202 with anchor members 204 pre-loaded on an inner sheath 207 is advanced and inserted into the left ventricle wall at the proximal boundary 274 of the ischemic tissue 272. The suture 212 is tightened as the crimp body 202 is locked in position by the anchor members 204 to pull the ends of the ischemic tissue 272 closer together.

Figure 16:
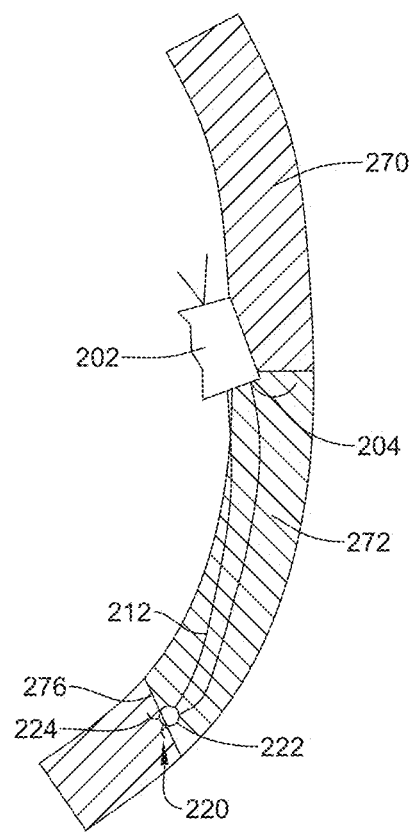
FIG. 16 is a cross sectional view of a device for improving cardiac function implanted in the heart.

In an alternative embodiment, instead of the external pledget 210 shown in FIG. 15, the securing member may be an internal anchor 220. The crimp body 202 may be connected to an internal anchor 220 with the suture 212, as shown in FIG. 16. The suture may be elastic or in the form of a spring such that after tightening, the suture continues to exert a tensile force pulling the tissue together. The internal anchor 220 is configured to be implanted within the heart wall and may prevent the potential for tamponade. The internal anchor 220 may have a suture eyelet 222 for connecting the suture 212, and a plurality of anchors 224, such as hooks or barbs. The internal anchor 220 may be deployed within the left ventricle wall through the inner needle 203 once the needle is shown via echocardiogram to be at the distal boundary 276 of the ischemic tissue 272.

The materials that can be used for the various components of the device 10, 100, 190, 200 for improving cardiac function, including the delivery catheter 5, inner shaft 7, central shaft 20, engagement element 30, dome structure 40, anchor members 50, and elongate members 60, etc. (and/or other systems or components disclosed herein) and the various elements thereof disclosed herein may include those commonly associated with medical devices. For simplicity purposes, the following discussion makes reference to the device 10, 100, the central shaft 20, the engagement element 30, the dome structure 40, the plurality of anchor members 50, and the elongate members 60, etc. However, this is not intended to limit the devices and methods described herein, as the discussion may be applied to other elements, members, components, or devices disclosed herein, such as, but not limited to, the spring members 160, patch 180, crimp body 202, anchor members 204, catheter 205, inner sheath 207, inner needle 203, etc. and/or elements or components thereof.

In some embodiments, at least one of the central shaft 20, the engagement element 30, the dome structure 40, the plurality of anchor members 50, and the elongate members 60, etc., and/or components thereof may be made from a metal, metal alloy, polymer (some examples of which are disclosed below), a metal-polymer composite, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the central shaft 20, the engagement element 30, the dome structure 40, the plurality of anchor members 50, and the elongate members 60, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the central shaft 20, the engagement element 30, the dome structure 40, the plurality of anchor members 50, and the elongate members 60, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the central shaft 20, the engagement element 30, the dome structure 40, the plurality of anchor members 50, and the elongate members 60, etc. to achieve the same result.

In some embodiments, a degree of Magnetic Resonance Imaging (MM) compatibility is imparted into the central shaft 20, the engagement element 30, the dome structure 40, the plurality of anchor members 50, and the elongate members 60, etc. For example, the central shaft 20, the engagement element 30, the dome structure 40, the plurality of anchor members 50, and the elongate members 60, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The central shaft 20, the engagement element 30, the dome structure 40, the plurality of anchor members 50, and the elongate members 60, etc., or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, at least one of the central shaft 20, the engagement element 30, the dome structure 40, the plurality of anchor members 50, and the elongate members 60, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the central shaft 20, the engagement element 30, the dome structure 40, the plurality of anchor members 50, and the elongate members 60, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, antiplatelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A device for improving cardiac function, comprising:
a dome structure having a top end with an engagement element disposed thereon, the dome structure moveable from a first inside out configuration to a second deployed configuration, the dome structure being biased in the second deployed configuration; and
a plurality of anchor members disposed around a bottom open end, opposite the top end of the dome structure;
wherein the dome structure includes a plurality of elongate members connected to a central shaft, the engagement element disposed on the central shaft, each elongate member having a free end, wherein at least one of the plurality of anchor members is disposed on the free end of each elongate member.

2. The device of claim 1, wherein the dome structure includes a cover.

3. The device of claim 1, wherein the engagement element is a corkscrew extending from the top end toward the bottom open end of the dome structure in the second deployed configuration.

4. The device of claim 1, wherein the dome structure is made of a shape memory metal.

5. The device of claim 1, further comprising a delivery catheter and an inner shaft slidingly disposed within the delivery catheter, wherein the dome structure is removably coupled to a distal end of the inner shaft in the first inside out configuration, wherein when the inner shaft is advanced out of a distal end of the delivery catheter, the dome structure automatically moves into the second configuration.

6. The device of claim 1, wherein the plurality of anchor members are barbs.

7. The device of claim 1, wherein the plurality of anchor members are hooks.

8. The device of claim 7, wherein when in the first inside out configuration, the hooks face outward away from a center of the dome structure, and when in the second deployed configuration, the hooks face inward toward the center of the dome structure.

9. The device of claim 1, further comprising:
a delivery catheter; and
an inner shaft slidingly disposed within the delivery catheter;
the central shaft removably coupled to a distal end of the inner shaft, the central shaft having the engagement element disposed thereon;
wherein the dome structure includes the plurality of elongate members having first ends fixed to the central shaft defining the top end of the dome structure, the plurality of elongate members automatically moveable from the first inside out configuration when constrained within the delivery catheter to the second deployed configuration when released from the delivery catheter, the plurality of elongate members being biased in the second deployed configuration, wherein the plurality of anchor members are disposed on second free ends of each of the plurality of elongate members.

10. The device of claim 9, wherein the plurality of elongate members are made of a shape memory material.

11. The device of claim 9, wherein the engagement element is a corkscrew extending distally from the central shaft.

12. The device of claim 9, wherein the plurality of anchor members are hooks, wherein when in the first inside out configuration, the hooks face outward away from a center of the dome structure, and when in the second deployed configuration, the hooks face inward toward the center of the dome structure.

13. A method for improving cardiac function, comprising:
inserting a distal end of a catheter into a patient's heart adjacent a region of heart wall to be treated, wherein the catheter includes an inner shaft slidable within the catheter and a dome structure removably coupled to a distal end of the inner shaft in a first inside out configuration, the dome structure having a top end with an engagement element disposed thereon and a plurality of anchor members disposed around a bottom open end of the dome structure, the dome structure moveable from the first inside out configuration to a second deployed configuration, the dome structure being biased in the second deployed configuration in which the dome structure defines a cavity;
advancing the inner shaft distally at least partially out of the distal end of the catheter;
fixing the engagement element on the dome structure to the heart wall in the region to be treated; and
withdrawing the catheter proximally from the dome structure, thereby allowing the dome structure to automatically move into the second deployed configuration, wherein movement of the dome structure into the second deployed configuration results in the anchor members engaging the heart wall and pulling the heart wall into the cavity defined by the dome structure.

14. The method of claim 13, wherein the engagement element is a corkscrew and fixing the engagement element to the heart wall includes rotating the inner shaft to screw the corkscrew into the heart wall.

15. The method of claim 13, wherein before inserting the catheter, the method includes applying a vacuum to an interior of the heart wall in the region to be treated to displace the heart wall inward, wherein fixing the engagement element to the heart wall includes fixing the engagement element to the displaced heart wall.

* * * * *